United States Patent [19]

Lohaus et al.

[11] 3,931,277
[45] Jan. 6, 1976

[54] NOVEL ISOCYANATES AND PROCESSES FOR THEIR PREPARATION

[75] Inventors: Gerhard Lohaus; Hilmar Mildenberger, both of Kelkheim, Taunus, Germany

[73] Assignee: Hoechst Aktiengesellschaft, Frankfurt am Main, Germany

[22] Filed: Nov. 20, 1973

[21] Appl. No.: 417,639

[30] Foreign Application Priority Data
Nov. 22, 1972 Germany............................ 2257240

[52] U.S. Cl....... 260/465 D; 260/309.2; 260/545 R; 260/543 R; 424/273
[51] Int. Cl.²..................................... C07C 143/128
[58] Field of Search ...... 260/545 R, 545 CA, 465 D

[56] References Cited
OTHER PUBLICATIONS
Weygand et al., Preparative Organic Chemistry 410411473.474, 678–680 (1972).

Primary Examiner—Robert Gerstl
Attorney, Agent, or Firm—Curtis, Morris & Safford

[57] ABSTRACT

Sulfonylamino-sulfonyl-isocyanates of the formula

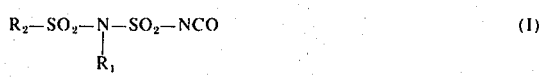

where $R_1$ is alkyl having from 1 to 12 carbon atoms, or cycloalkyl having from 4 to 8 carbon atoms, and $R_2$ is alkyl or halogeno-alkyl, each having from 1 to 20 carbon atoms, cycloalkyl having from 5 to 8 carbon atoms; phenyl, benzyl or naphthyl optionally substituted by halogen, alkyl or alkoxy each having from 1 to 4 carbon atoms, cyano and/or nitro.

5 Claims, No Drawings

NOVEL ISOCYANATES AND PROCESSES FOR THEIR PREPARATION

The present invention provides sulfonylamino-sulfonylisocyanates of the formula

where $R_1$ is alkyl having from 1 to 12 carbon atoms, or cycloalkyl having from 4 to 8 carbon atoms, and $R_2$ is alkyl or halogeno-alkyl, each having from 1 to 20 carbon atoms; cycloalkyl having from 5 to 8 carbon atoms; phenyl, benzyl or naphthyl optionally substituted by halogen, alkyl or alkoxy each having from 1 to 4 carbon atoms, cyano and/or nitro.

Preferred radicals, $R_1$ are alkyl having from 1 to 6 carbon atoms, especially alkyl having from 1 to 4 carbon atoms, and cycloalkyl having from 4 to 6 carbon atoms, especially cyclohexyl.

Preferred radicals $R_2$ are alkyl having from 1 to 12 carbon atoms, cyclohexyl, methylphenyl, chlorophenyl, fluorophenyl or nitrophenyl.

The present invention provides also a process for the preparation of compounds of formula I, which comprises reacting sulfonamides of the formula $$R_2SO_2-NH-R_1 \qquad (II)$$

with chlorosulfonyl-isocyanate.

The reaction in accordance with the present invention may be carried out in one or two steps. It is possible, for example, to prepare first the addition product of the formula

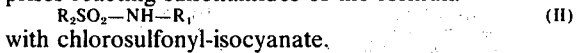

starting from the sulfonamide II and chlorosulfonyl-isocyanate, at low temperature of from about 0° to 80°C, and subsequently convert this product to the isocyanate of formula I by heating, or the components may be heated from the start to the temperature required for the reaction in accordance with the present invention. Also an excess of the chlorosulfonyl-isocyanate of up to 100 % of the theoretical amount or more may be used. The reaction temperatures are generally from 80° to 200°C, preferably from 100° to 160°C.

The reaction may be carried out without solvent. However, it is generally advantageous to add a solvent or diluent indifferent under the reaction conditions, preferably hydrocarbons which may also be substituted by halogen atoms or nitro groups having boiling points above about 80°C, when the reaction is to be carried out without pressure. Such solvents or diluents are preferably the following: aliphatic or cycloaliphatic hydrocarbons having more than 6 carbon atoms, aliphatic or cycloaliphatic hydrocarbons substituted by nitro groups or halogen atoms having a boiling point of at least 80°C, but especially aromatic hydrocarbons which may also be substituted by halogen, nitro groups or alkyl radicals, for example benzene, toluene, xylene, ethylbenzene, isopropylbenzene, tetrahydro-naphthalene, diisopropylbenzene, chlorobenzene, dichlorobenzene, chlorotoluene, chloroxylene or nitrobenzene.

In the reaction according to the present invention, hydrogen chloride is set free which escapes in gaseous form. Surprisingly, it is not necessary to bind it chemically in order to ensure the desired course of the reaction, as is required for many other reactions which proceed with splitting off of hydrogen halides. It may be advantageous, however, to accelerate the release of the hydrogen chloride formed, for example by passing an inert gas such as nitrogen through the reaction vessel, or by applying a slight vacuum. By titrimetric determination, of the hydrogen chloride split off, the course of the reaction may be quantitatively monitored and thus its completion can be verified.

In most cases, the new sulfonyl-isocyanates are liquid compounds which can be distilled under reduced pressure. Therefore, they are generally and advantageously isolated by distillation. In many cases, however, this isolation is not necessary; the reaction product may be used directly for further reactions after removal of excess chlorosulfonyl-isocyanate (for example by distillation) and, optionally, of the solvent employed. This applies especially for those isocyanates of formula I which because of their size of molecules or their high boiling point are difficult to distill without decomposition.

The process of the invention and its products are new. Since it is known (Chem. Ztg. — Chem. Appar. 95 (1971), 1009) that perfluorinated alkyl-sulfonamides do not react with chlorosulfonyl-isocyanate to form sulfonylamino-sulfonyl-isocyanates, but from normal sulfonyl-isocyanates having only one sulfonyl group in the molecule together with sulfamic acid chloride as by-product, it is surprising that the compounds of formula II react in an entirely different manner.

Isocyanates which can be prepared in accordance with the process of the present invention are for example: methanesulfonyl-n-propylamino-sulfonylisocyanate, methanesulfonyl-isopropylamino-sulfonylisocyanate, methanesulfonyl-n-octylamino-sulfonylisocyanate, methanesulfonyl-cyclobutylamino-sulfonylisocyanate, methanesulfonyl-cyclopentylamino-sulfonylisocyanate, methanesulfonyl-cyclohexylamino-sulfonylisocyanate, methanesulfonyl-4-methylcyclohexylamino-sulfonylisocyanate, ethanesulfonyl-n-butylamino-sulfonylisocyanate, ethanesulfonyl-isopropylamino-sulfonylisocyanate, n-butanesulfonyl-isopropylamino-sulfonylisocyanate, n-butanesulfonyl-cyclohexylamino-sulfonylisocyanate, dodecanesulfonyl-methylamino-sulfonylisocyanate, octadecanesulfonyl-methylamino-sulfonylisocyanate, 2-chloroethanesulfonyl-ethyl-amino-sulfonylisocyanate, cyclopentanesulfonyl-ethylamino-sulfonylisocyanate, cyclohexanesulfonyl-butylamino-sulfonylisocyanate, 4-methylcyclohexanesulfonyl-methylamino-sulfonylisocyanate, cyclooctanesulfonyl-methylamino-sulfonylisocyanate, benzylsulfonyl-methylamino-sulfonylisocyanate, phenylsulfonyl-ethylamino-sulfonylisocyanate, 4-toluenesulfonyl-methylamino-sulfonylisocyanate, phenylsulfonyl-cyclohexylamino-sulfonylisocyanate, 2,4-dimethylphenylsulfonyl-ethylamino-sulfonylisocyanate, 3,4-dimethylphenylsulfonyl-ethylamino-sulfonylisocyanate, 4-ethylphenylsulfonyl-methylamino-sulfonylisocyanate, 4-isopropylphenylsulfonyl-methylamino-sulfonylisocyanate, 3-chlorophenylsulfonyl-methylamino-sulfonylisocyanate, 4-bromophenylsulfonyl-methylamino-sulfonylisocyanate, 2,5-dichlorophenylsulfonyl-methylamino-sulfonylisocyanate, 3-chloro-4-methyl-phenylsulfonyl-methylamino-sulfonylisocyanate, 3-nitrophenylsulfonyl-methylamino-sulfonylisocyanate, 3-nitro-4-methylphenylsulfonyl-methylamino-sulfonylisocyanate, 2-chloro-5-nitro-phenylsulfonyl-methylamino-sulfonylisocyanate, 4-methoxy-phenylsulfonyl-methylamino-sulfonylisocyanate, 3-cyanophenylsulfonyl-methylamino-sulfonylisocyanate, 1-naphthylsulfonyl-methylamino-sulfonylisocyanate, 1-chloro-6-naphthylsulfonyl-methylamino-sulfonylisocyanate.

The sulfonylamino-sulfonyl-isocyanates obtained in accordance with the present invention may be used as reactive intermediate products for syntheses of various kinds. Especially, when these sulfonyl-isocyanates are reacted wth benzimidazolecarbamates, products having an excellent fungicidal and anthelmintic activity are formed, which products correspond to the formual

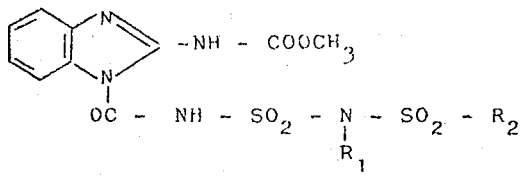

The preparation and the properties are described in our copending application Ser. No. 417640 (German Application No. P 22 57 184.2)

The following examples illustrate the invention.

EXAMPLE 1 a. 151 g (1.38 moles) of methanesulfonic acid methyl amide are dissolved in 500 ml of chlorobenzene, a solution of 215 g (1.52 moles) of chlorosulfonyl-isocyanate in 200 ml of chlorobenzene is added within 10 minutes at room temperature, the whole is subsequently heated at 120° – 125°C for 4 hours with agitation, and finally, the methanesulfonyl-methylamino-sulfonylisocyanate is isolated by distillation. The yield is 173 g (59 %), boiling point 94° – 98°C/0.1 torr.

| $C_3H_6N_2O_5S_2$ | MW 214.2 |
|---|---|
| calc.: N 13.1 %; | S 29.9 % |
| found: N 13.0 %; | S 30.0 % |

By hydrolizing this product with water, methylsulfonyl-methylamino-sulfonamide having a melting point of 140°C is formed.

Under the above conditions, the following isocyanates are obtained from the corresponding sulfonamides:

b. methanesulfonyl-butylamino-sulfonylisocyanate, yield 62 %, boiling point 106° – 112°C/0.05 torr

| $C_6H_{12}N_2O_5S_2$ | MW 256.3 |
|---|---|
| calc.: N 10.9 %; | S 25.0 % |
| found: N 10.6 %; | S 24.8 % | c. ethanesulfonyl-ethylamino-sulfonylisocyanate, yield 64 %, boiling point 95° – 99°C/0.01 torr

| $C_5H_{10}N_2O_5S_2$ | MW 242.3 |
|---|---|
| calc.: N 11.6 %; | S 26.4 %; |
| found: N 11.8 %; | S 26.8 % | d. butanesulfonyl-methylamino-sulfonylisocyanate, yield 53 %, boiling point 110° – 116°C/0.1 torr

| $C_6H_{12}N_2O_5S_2$ | MW 256.3 |
|---|---|
| calc.: N 10.9 %; | S 25.0 % |
| found: N 10.8 %; | S 25.4 % |

EXAMPLE 2 a. 225 g (1.60 moles) of chlorosulfonyl-isocyanate are added to a solution of 170 g (1.38 moles) of methanesulfonic acid ethylamide in 700 ml of chlorobenzene, and the whole is heated for 5 hours at a bath temperature of 150°C while passing nitrogen through the reaction vessel. Subsequently, 256 g (81 %) of methanesulfonyl-ethylamino-sulfonylisocyanate having a boiling point of 99° – 106°C/1 torr are isolated by distillation.

| $C_4H_8N_2O_5S_2$ | MW 228.2 |
|---|---|
| calc.: N 12.3 %; | S 28.1 % |
| found: N 12.5 %; | S 28.6 % |

Under the same reaction conditions, the following sulfonyl-isocyanates are obtained from the corresponding sulfonamides:

b. cyclohexanesulfonyl-methylamino-sulfonylisocyanate, yield 39 %, boiling point 120° – 124°C/0.02 torr

| $C_8H_{14}N_2O_5S_2$ | MW 282.3 |
|---|---|
| calc.: N 9.9 %; | S 22.7 % |
| found: N 9.7 %; | S 23.1 % | c. ethanesulfonyl-methylamino-sulfonylisocyanate, yield 68 %, boiling point 103° – 105°C/0.05 torr

| $C_4H_8N_2O_5S_2$ | MW 228.2 |
|---|---|
| calc.: N 12.3 %; | S 28.1 % |
| found: N 12.0 %; | S 28.4 % | d. n-butanesulfonyl-ethylamino-sulfonylisocyanate, yield 70 %, boiling point 98° – 103°C/0.01 torr

| $C_7H_{14}N_2O_5S_2$ | MW 270.3 |
|---|---|
| calc.: N 10.4 %; | S 23.7 % |
| found: N 10.1 %; | S 23.9 % | e. 2-chloroethanesulfonyl-methylamino-sulfonylisocyanate, yield 38 %, boiling point 105° – 110°C/0.02 torr

| $C_4H_7ClN_2O_5S_2$ | MW 262.7 |
|---|---|
| calc.: N 10.7 %; | S 24.4 % |
| found: N 10.9 %; | S 24.0 % | f. octanesulfonyl-methylamino-sulfonylisocyanate, yield 59 %, boiling point 134° – 137°C/0.01 torr

| $C_{10}H_{20}N_2O_5S_2$ | MW 312.4 |
|---|---|
| calc.: N 9.0 %; | D 20.5 % |
| found: N 8.7 %; | S 20.9 % |

EXAMPLE 3 a. 44 g (0.31 mole) of chlorosulfonyl-isocyanate are added to a solution of 50 g (0.29 mole) of benzenesulfonic acid methylamide in 150 ml of chlorobenzene, and the whole is heated at 120°C for 4 hours with agitation. The distillation yields 47 g (58 %) of phenylsulfonyl-methylaminosulfonylisocyanate having a boiling point of 125°–128°C/0.03 torr.

| $C_8H_8N_2O_5S_2$ | MW 276.3 |
|---|---|
| calc.: N 10.1 %; | S 23.2 % |
| found: N 10.5 %; | S 23.6 % |

In the same manner, the following wulfonylisocyanates are obtained from the corresponding sulfonamides:

b. 4-chlorophenylsulfonyl-methylamino-sulfonylisocyanate, yield 90 %, boiling point 140°–145°C/0.02 torr

| $C_8H_7ClN_2O_5S_2$ | MW 310.8 |
|---|---|
| calc.: N 9.1 %; | S 20.6 % |
| found: N 9.3 %; | S 20.7 % | c. 4-chlorophenylsulfonyl-ethylamino-sulfonylisocyanate, yield 92 %, boiling point 146°–149°C/0.01 torr

| $C_9H_9ClN_2O_5S_2$ | MW 324.8 |
|---|---|
| calc.: N 8.6 %; | S 19.7 % |
| found: N 8.5 %; | S 19.2 % | d. 4-chlorophenylsulfonyl-butylamino-sulfonylisocyanate, yield 89 %, boiling point 148°–150°C/0.01 torr

| $C_{11}H_{13}ClN_2O_5S_2$ | MW 352.8 |
|---|---|
| calc.: N 7.9 %; | S 18.2 % |
| found: N 7.6 %; | S 18.3 % | e. 4-nitrophenylsulfonyl-cyclohexylamino-sulfonylisocyanate, yield 83 %, boiling point 167°–170°C/0.005 torr (partial decomp.)

| $C_{13}H_{15}N_3O_7S_2$ | MW 389.4 |
|---|---|
| calc.: N 10.8 %; | S 16.4 % |
| found: N 10.5 %; | S 16.4 % | f. 4-nitrophenylsulfonyl-propylamino-sulfonylisocyanate, yield 85 %, boiling point 156°–159°C/0.01 torr (partial decomp.)

| $C_{10}H_{11}N_3O_7S_2$ | MW 349.3 |
|---|---|
| calc.: N 12.0 %; | S 18.3 % |
| found: N 11.8 %; | S 18.5 % | g. 2,4-dimethylphenylsulfonyl-methylamino-sulfonylisocyanate, yield 63 %, boiling point 130°–135°C/0.01 torr

| $C_{10}H_{12}N_2O_5S_2$ | MW 304.3 |
|---|---|
| calc.: N 9.2 %; | S 21.1 % |
| found: N 8.8 %; | S 20.9 % | h. 4-fluorophenylsulfonyl-methylamino-sulfonylisocyanate, yield 61 %, boiling point 118°–122°C/0.02 torr

| $C_8H_7FN_2O_5S_2$ | MW 294.3 |
|---|---|
| calc.: N 9.5 %; | S 21.8 % |
| found: N 9.5 %; | S 21.6 % | i. 3-chloro-4-methyl-phenylsulfonyl-methylaminosulfonylisocyanate, yield 68 %, boiling point 138°–142°C/0.01 torr

| $C_9H_9ClN_2O_5S_2$ | MW 324.8 |
|---|---|
| calc.: N 8.6 %; | S 19.7 % |
| found: N 8.3 %; | S 19.4 % | k. 4-tolylsulfonyl-butylamino-sulfonylisocyanate, yield 85 %, boiling point 138°–140°C/0.01 torr

| $C_{12}H_{16}N_2O_5S_2$ | MW 332.4 |
|---|---|
| calc.: N 8.4 %; | S 19.3 % |
| found: N 8.1 %; | S 19.1 % | l. phenylsulfonyl-isopropylamino-sulfonylisocyanate, yield 46 %, boiling point 121°–124°C/0.01 torr

| $C_{10}H_{12}N_2O_5S_2$ | MW 304.3 |
|---|---|
| calc.: N 9.2 %; | S 21.1 % |
| found: N 8.8 %; | S 21.1 % | m. 4-chlorophenylsulfonyl-cyclohexylamino-sulfonylisocyanate, yield 88 %, boiling point 153°–155°C/0.005 torr (slight decomp.)

| $C_{12}H_{15}ClN_2O_5S_2$ | MW 378.8 |
|---|---|
| calc.: N 7.4 %; | S 16.9 % |
| found: N 7.7 %; | S 16.5 % |

EXAMPLE 4

By reaction of 4-toluenesulfonic acid ethylamide with chlorosulfonylisocyanate in benzene, the crystalline addition product N-ethyl-N-chlorosulfonyl-amidocarbenyl-toluene-4-sulfonic acid amide is obtained.

102 g (0.3 mole) of this compound are heated at 100°C for 7 hours in 300 ml of 4-chlorotoluene, while passing nitrogen through the reaction vessel. By means of a subsequent distillation, 51 g (56 %) of 4-toluenesulfonyl-ethylamino-sulfonylisocyanate, having a boiling point of 123°–128°C/0.01 torr, are obtained.

| $C_{10}H_{12}N_2O_5S_2$ | MW 304.3 |
|---|---|
| calc.: N 9.2 %; | S 21.1 % |
| found: N 8.8 %; | S 20.9 % |

EXAMPLE 5

27.7 g (0.10 mole) of dedecanesulfonic acid ethylamide are heated for 5 hours at 130°C with 15 g (0.106 mole) of chlorosulfonyl-isocyanate, while passing dry nitrogen through the reaction vessel. Subsequently, all volatile components are distilled off at 0.01 torr and a bath temperature raised up to 120°C. The residue is composed of 36.9 g of a viscous oil.

| $C_{15}H_{30}N_2O_5S_2$ | MW 382.5 |
|---|---|
| calc.: N 7.3 %; | S 16.8 % |
| found: N 6.9 %; | S 16.2 % |

The isocyanate structure of the reaction product is proved by the sharp IR band at 4.4 $\mu$, and the violent

What is claimed is:

1. Sulfonylamino-sulfonyl-isocyanates of the formula $$R_2-SO_2-N(R_1)-SO_2-NCO \qquad (I)$$

where $R_1$ is alkyl having from 1 to 12 carbon atoms, or cycloalkyl having from 4 to 8 carbon atoms, and $R_2$ is alkyl or halogeno-alkyl, each having from 1 to 20 carbon atoms; cycloalkyl having from 5 to 8 carbon atoms; phenyl, benzyl or naphthyl optionally substituted by halogen, alkyl or alkoxy each having from 1 to 4 carbon atoms, cyano and/or nitro.

2. A process for the preparation of compounds of formula I, which comprises reacting sulfonamides of the formula $$R_2SO_2-NH-R_1 \qquad (II)$$

in which $R_1$ and $R_2$ are as defined in claim 1, with chlorosulfonyl-isocyanate at a temperature from 80° to 200°C.

3. A process as claimed in claim 2, which comprises carrying out the reaction at a temperature of from 100° to 160°C.

4. A process as claimed in claims 2, which comprises carrying out the reaction in the presence of an inert solvent or diluent.

5. In a process for reacting sulfonamides of the general formula $$R_2-SO_2-NH-R_1 \qquad (II)$$

in which $R_1$ and $R_2$ are as defined in claim 1 to obtain the compounds of formula $$R_2-SO_2-N(R_1)-SO_2-NCO \qquad (I)$$

whereby compound of the formula II is reacted with chlorosulfonyl isocyanate at a temperature of from 0° to 80°C to form sulfochlorides of the general formula $$R_2-SO_2-N(R_1)-CO-NH-SO_2Cl \qquad (III)$$

the step comprising rearranging the intermediate products of formula III to compounds of formula I by heating said compounds of formula III at a temperature from 80°C to 200°C.

* * * * *